United States Patent

Hamprecht et al.

Patent Number: 5,280,118
Date of Patent: Jan. 18, 1994

[54] TRIFLUORO- AND CHLORODIFLUOROMETHOXY-1,3,5-TRIAZINES

[75] Inventors: Gerhard Hamprecht, Weinheim; Horst Mayer, Ludwigshafen; Hans-Josef Wolf, Maxdorf, all of Fed. Rep. of Germany

[73] Assignee: BASF Aktiengesellschaft, Ludwigshafen, Fed. Rep. of Germany

[21] Appl. No.: 985,119

[22] Filed: Dec. 3, 1992

Related U.S. Application Data

[62] Division of Ser. No. 736,229, Jul. 26, 1991, Pat. No. 5,194,610.

[30] Foreign Application Priority Data

Aug. 3, 1990 [DE] Fed. Rep. of Germany ....... 4024755

[51] Int. Cl.⁵ .................. C07D 251/16; C07D 251/26
[52] U.S. Cl. ...................................... 544/218; 544/219
[58] Field of Search ................................ 544/219, 218

[56] References Cited

U.S. PATENT DOCUMENTS

3,525,745  8/1970  Anderson ............................ 260/248
4,443,243  4/1984  Forg et al. ............................ 71/93

FOREIGN PATENT DOCUMENTS

0070804  1/1983  European Pat. Off.

OTHER PUBLICATIONS

Suzuki et al., Chemical Abstracts, vol. 60, entry 2986d (1964).
Hamprecht et al., Chemical Abstracts, vol. 116, entry 235659z (1992).
Chemical Abstract, vol. 60, 2986d, (1964) M. Suzuki, et al., "Triazine Derivatives", Japan. 17,039, Sep. 4, 1963.
The Journal of the American Chemical Society, vol. 81, Jul. 20, 1959, E. Kober, et al., "Triazines. XXII. Fluoro-s-Triazines", pp. 3769-3770.

*Primary Examiner*—John M. Ford
*Attorney, Agent, or Firm*—Oblon, Spivak, McClelland, Maier & Neustadt

[57] ABSTRACT

Trifluoro- and chlorodifluoromethoxy-1,3,5-triazines of the formula I

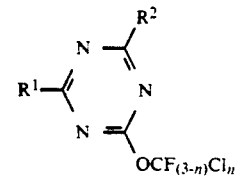

where $R^1$ and $R^2$ are each, independently of one another, hydrogen, halogen or $C_1$-$C_4$-haloalkyl, and $R^1$ is also trifluoro- or chlorodifluoromethoxy, and n is 0 or 1, excepting 2,4-dichloro-6-trifluoromethoxy-1,3,5-triazine, are prepared as described.

2 Claims, No Drawings

TRIFLUORO- AND CHLORODIFLUOROMETHOXY-1,3,5-TRIAZINES

This is a division of application Ser. No. 07/736,229, filed on Jul. 26, 1991, now U.S. Pat. No. 5,194,610.

The present invention relates to a process for preparing substituted trifluoro- and chlorodifluoro-methoxy-1,3,5-triazines, some of which are novel, of the formula I

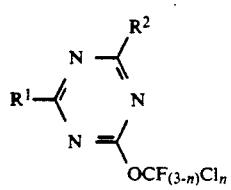

where $R^1$ and $R^2$ are each, independently of one another, hydrogen, halogen or haloalkyl, and $R^1$ is also trifluoro- or chlorodifluoromethoxy, and n is 0 or 1, and the novel products of the formula I excepting 2,4-dichloro-6-trifluoromethoxy-1,3,5-triazine.

The present invention also relates to the compounds II and a process for the preparation thereof.

Compounds I and II are used as intermediates for preparing drugs, dyes and crop protection agents, especially for preparing herbicidal sulfonylurea derivatives.

Because of the difficulty of handling the extremely reactive, unselective and toxic fluorine, to date no methods for the direct fluorination of alkoxy-1,3,5-triazines have been disclosed. U.S. Pat. No. 3 525 745 describes the preparation of 2,4-dichloro-6-trifluoromethoxy-1,3,5-triazine by reacting toxic carbonyl fluoride with potassium fluoride in acetonitrile, followed by reaction with cyanuric chloride. This known process is not economic because of the low yields (6.1% of theory), the use of an autoclave, the long reaction times which are more than 20 hours in each reaction step, the complicated work-up and the disposal of numerous by-products. EP-A 70804 describes the reaction of 2-amino-4-mercapto-6-methoxy-1,3,5-triazine with chlorodifluoromethane to give the corresponding 6-difluoromethylthio compound. The yield of 24% is unsatisfactory in this case too; moreover, because of the higher nucleophilicity of the mercapto group compared with the hydroxyl group, it has been possible to use the process only for preparing fluoroalkylthio- but not fluoroalkoxy-1,3,5-triazines. Finally, special safety measures are required when handling harmful chlorodifluoromethane in order to prevent it escaping into the atmosphere.

It is an object of the present invention to prepare the fluoromethoxy-1,3,5-triazines according to the invention in a way which, compared with the prior art, is more straightforward, has shorter reaction times and gives better yields, and is highly selective, not involving the exchange of several nuclear halogen atoms.

We have found that this object is achieved by preparing the novel trifluoro- and chlorodifluoromethoxy-1,3,5-triazines of the formula I

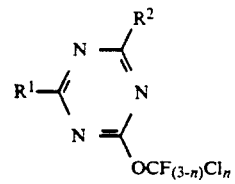

where $R^1$ and $R^2$ have the abovementioned meanings, by carrying out halogen replacement on trichloromethoxy-1,3,5-triazines of the formula II

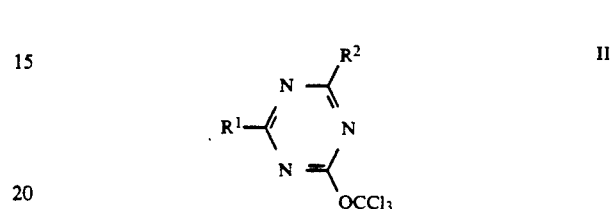

where $R^1$ and $R^2$ are each, independently of one another, hydrogen, fluorine or $C_1$–$C_4$-haloalkyl, and $R^1$ is also trichloromethoxy.

Suitable for the halogen replacement are antimony trifluoride in the presence or absence of catalytic amounts of an antimony(V) salt, e.g. antimony(V) chloride, or hydrogen fluoride.

The reaction of 2,4-difluoro-6-trichloromethoxy-1,3,5-triazine and antimony trifluoride and a catalytic amount of antimony pentachloride, or hydrogen fluoride, can be represented as follows:

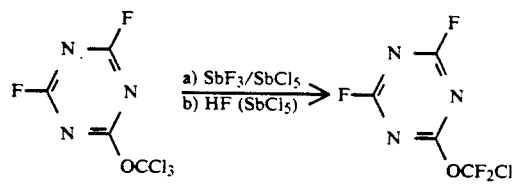

The reaction with antimony trifluoride or hydrogen fluoride and a larger catalytic amount of antimony pentachloride can be represented as follows:

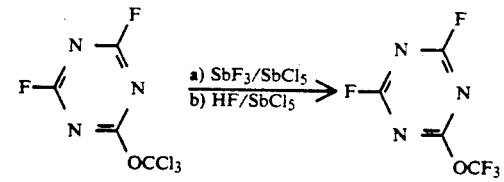

The reaction of 2,4-dichloro-6-trichloromethoxy-1,3,5-triazine can be represented as follows:

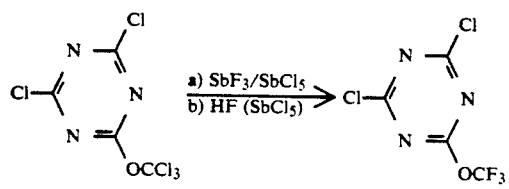

The process provides in a straightforward and economic way novel trifluoromethoxy- and chlorodifluoromethoxy-1,3,5-triazines in high yield and purity. Chlorine atoms on the nucleus are not replaced in this reaction. In view of the prior art, all these advantageous properties are surprising.

With a view to further processing to give herbicidal sulfonylurea derivatives, the preferred products I and, accordingly, preferred starting materials II are those where $R^1$ and $R^2$ are each, independently of one another, hydrogen, fluorine, chlorine, bromine, trichloromethyl, dichlorofluoromethyl, chlorodifluoromethyl, trifluoromethyl, 1,1-dichloro-2,2,2-trifluoroethyl, 1,1,2,2,2-pentafluoroethyl and 1,1,2,2,2-pentachloroethyl and, additionally, those products I where $R^1$ is additionally trifluoromethoxy or chlorodifluoromethoxy when $R^1$ in the corresponding starting materials II is trichloromethoxy, dnd n is 0 or 1.

It is expedient to use an excess of from 1 to 200, preferably 5 to 25, mol % of antimony trifluoride per trichloromethyl equivalent. The catalytic amount of antimony(V) salt is from 1 to 20, preferably 5 to 18, mol % per trichloromethyl equivalent. The starting material II is preferably metered at from 90° to 130° C. into the mixture containing the agent for halogen replacement, and the mixture is then heated at from 110° to 180° C. for from 10 to about 240 minutes. Subsequent working up is by distillation.

However, the reaction can also be carried out continuously, adding the starting material II at from 110 to 180° C. over the course of from 10 to about 240 minutes and, at the same time, removing the lower boiling product I by distillation under reduced pressure. Traces of antimony salts which are carried over can be removed by extraction with concentrated hydrochloric acid.

The halogen replacement remains at the chlorodifluoromethoxy stage if no antimony(V) salt is used for catalysis or if only small amounts, e.g. from 0.5 to 5 mol %, are employed and the amount of antimony trifluoride is reduced to from 60 to 90 mol % per trichloromethyl equivalent.

The halogen replacement can also be carried out with hydrogen fluoride, in place of antimony trifluoride, at from 0° to 150° C., preferably 40° to 120° C. For this purpose, an excess of from 300 to 700, preferably 350 to 400, mol % of hydrogen fluoride per trichloromethyl equivalent is added to the starting material II in an autoclave, and the mixture is then stirred for from 10 minutes to about 10 hours. The reaction rate can be increased in the same way as described for the use of antimony trifluoride, i.e. by addition of a catalyst such as antimony pentachloride. A reaction time of up to 4 hours is generally sufficient. After release of pressure and removal of volatile constituents, working up is carried out as described.

Preferred products of the formula I with a view to their further processing to give herbicidal sulfonylurea derivatives are, for example, 2-fluoro-4-trifluoromethoxy-1,3,5-triazine, 4-chloro-2-trifluoromethoxy-1,3,5-triazine, 2,4-bis-trifluoromethoxy-1,3,5-triazine, 2,4-difluoro-6-trifluoromethoxy-1,3,5-triazine, 6-chlorodifluoromethoxy-2,4-difluoro-1,3,5-triazine, 2,4-dichloro-6-trifluoromethoxy-1,3,5-triazine, 6-chlorodifluoromethoxy-2,4-dichloro-1,3,5-triazine, 2-chloro-4,6-bis-chlorodifluoromethoxy-1,3,5-triazine, 2,4-bis-trifluoromethoxy-6-chloro-1,3,5-triazine, 2-chloro-4-trifluoromethoxy-6-trifluoromethyl-1,3,5-triazine, 2-fluoro-4-trifluoromethoxy-6-trifluoromethyl-1,3,5-triazine, 4-chlorodifluoromethoxy-2-fluoro-6-trifluoromethyl-1,3,5triazine and 2,4-bis-trifluoromethoxy-6-trifluoromethyl-1,3,5-triazine.

The trichloromethoxy-1,3,5-triazines of the formula II which are required for the preparation of the fluorinated 1,3,5-triazines I

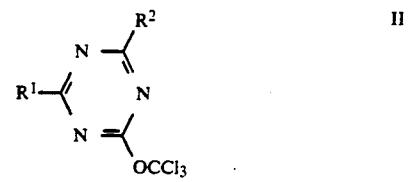

where $R^1$ and $R^2$ have the meanings mentioned in the first paragraph, are advantageously obtained by chlorinating methoxy-1,3,5-triazines of the formula III

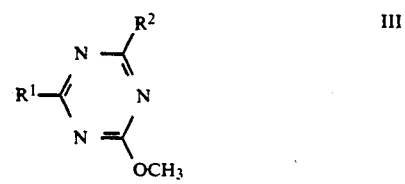

where $R^1$ and $R^2$ are each, independently of one another, hydrogen, fluorine or $C_1$-$C_4$-haloalkyl, and $R^1$ is also methoxy.

The chlorination can be carried out by a relatively old process described in Japanese Laid-Open Application 17 039 ('63); Chemical Abstracts 60, 2986 d, in which case it is necessary to use tetrachloromethane as solvent. The latter is a very toxic solvent which, according to current views on worker safety, should not be used (Merkblätter Gefährliche Arbeitsstoffe, Verlag Moderne industrie, W. Dummer & Co., Munich, 1977). Tetrachloromethane is also carcinogenic (Roth +Daunderer Giftliste, 8th Supplement 12/80; 1979 ecomed Verlagsgesellschaft, Landsberg). In addition, the known process involves very elaborate procedures and purification steps. Thus, for example, in the first stage 2,4-dichloro-6-methoxy-1,3,5-triazine is chlorinated to 2-chloromethoxy-4,6-dichloro-1,3,5-triazine, which must be distilled and purified by recrystallization (Example 1). Then, in another step, chlorination is carried out to give the trichloromethoxy compound, which itself has to be distilled and purified by recrystallization (Example 6). Only the crude yields, not the yields after purification, are stated. On the other hand, chlorination at elevated temperatures will be expected, by analogy with the chlorination of 2,4-dichloro-6-methyl-1, 3,5-triazine, to give unsatisfactory yields of product because of the formation of a tetrachloroethane by-product which will have to be removed by an elaborate sequence of extraction, distillation, crystallization and sublimation processes (J. Amer. Chem. Soc. 81 (1959) 3769).

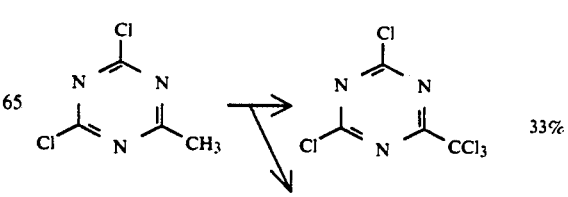

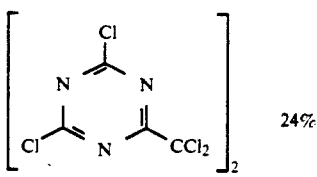

24%

We have now found, surprisingly, that 2,4-difluoro-6-trichloromethoxy-1,3,5-triazines can be obtained in high yields, in one step, without interfering side reactions and with straightforward working up when the chlorination is carried out at elevated temperatures, e.g. from 100° to 180° C.

The chlorination of 2,4-difluoro-6-methoxy-1,3,5triazine with chlorine can be represented as follows.

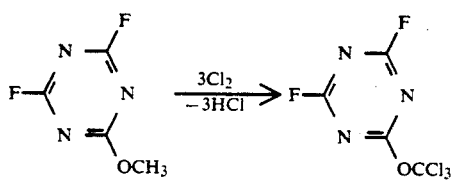

The process provides in a straightforward and economic manner novel trichloromethoxytriazines in high yield and purity.

Preferred intermediates II and, accordingly, preferred starting materials III are those where $R^1$ and $R^2$ are each, independently of one another, hydrogen, fluorine, trichloromethyl, dichlorofluoromethyl, chlorodifluoromethyl, trifluoromethyl, 1,1-dichloro-2,2,2-trifluoroethyl, 1,1,2,2,2-pentafluoroethyl and 1,1,2,2,2pentachloroethyl and, in addition, those products II where $R^1$ is additionally trichloromethoxy when $R^1$ in the corresponding starting materials is methoxy.

Suitable for the chlorination are elemental chlorine or chlorine-releasing substances such as sulfuryl chloride or phosphorus pentachloride. Chlorine can also be prepared in situ by oxidation of hydrogen chloride, for example with hydrogen peroxide.

The reaction can be carried out in the presence of an inert, high-boiling solvent, for example a chlorohydrocarbon such as chlorobenzene, 1,2-, 1,3- or 1,4-dichlorobenzene, a nitro compound such as nitrobenzene, a carboxylic acid such as acetic acid or propionic acid, an anhydride such as acetic anhydride, an acid chloride such as chloroacetyl chloride, α-chloropropionyl chloride or α,α-dichloropropionyl chloride, an inorganic acid halide such as phosphorus trichloride or phosphorus oxychloride or, preferably, without solvent in a melt of the starting material III.

The reaction rate may be increased by use of a radical initiator, those suitable being irradiation with light, preferably UV light, or addition of α,α'-azoisobutyronitrile, expediently in an amount of from 0.2 to 7 mol % based on the starting material III. The reaction rate can also be increased by adding a catalyst; suitable for this is phosphorus pentachloride, expediently in an amount of from 0.5 to 7 mol % based on starting material III. In this case, the starting material and catalyst are mixed and then the chlorination is started. In place of phosphorus pentachloride it is also possible to add starting components which form the latter under the reaction conditions, e.g. phosphorus trichloride or yellow phosphorus, and then to start the chlorination.

Starting material III can be reacted with chlorine in approximately the stoichiometric amount or, preferably, in excess, advantageously from 3.1 to 11, in particular 3.3 to 5, moles of chlorine per methoxy equivalent in the starting material III. The reaction is carried out at from 100° to 180° C., advantageously from 120° to 150° C., under atmospheric or superatmospheric pressure, continuously or batchwise.

If the chlorination is carried out under 1 bar, it is expedient to use from 3.3 to 5 moles of gaseous chlorine per methoxy equivalent in the starting material III, which corresponds to a chlorine conversion of from 91 to 60%. The chlorine conversion can be increased by appropriate measures, e.g. by use of moderate pressure, expediently from 1 to 10 bar, or by using a bubble column. It is advantageous to allow the gaseous chlorine to stay in contact with the organic phase for as long as possible by, for example, vigorously stirring the latter or forcing the chlorine to pass through a thick layer of the organic phase.

The reaction generally takes from about 0.5 to 12 hours.

The procedure in a preferred embodiment of the process is to pass the required amount of gaseous chlorine into the vigorously stirred liquid starting material III over the course of from 0.5 to 12 hours, preferably 1 to 10 hours, starting at from 120° to 130° C. and raising the temperature continuously, where appropriate by utilizing the exothermic nature of the reaction, until it is at from 135° to 150° C. toward the end of the reaction. It is obvious that for larger batches the exothermic nature of the reaction must be taken into account by external cooling or suitable metering of the chlorine; when the reaction subsides the cooling bath is removed and, where appropriate, heat is then applied.

The products can be worked up and isolated in a conventional manner. For example, residual hydrogen chloride, chlorine or catalyst can be driven out of the hot organic phase using an inert gas; this leaves behind a high yield of crude product which is already rather pure. It can be further purified by distillation or chromatography, or else used immediately for further reactions.

Examples of preferred products of the formula II are 2-fluoro-4-trichloromethoxy-1,3,5-triazine, 4-chloro-2-trichloromethoxy-1,3,5-triazine, 2,4-bis-trichloromethoxy-1,3,5-triazine, 2,4-difluoro-6-trichloromethoxy-1,3,5-triazine, 2-fluoro-4,6-bis-trichloromethoxy-1,3,5triazine, 2,4-dichloro-6-trichloromethoxy-1,3,5-triazine, 2-chloro-4,6-bis-trichloromethoxy-1,3,5-triazine, 2-chloro-4-trichloromethoxy-6-trichloromethyl-1,3,5-triazine, 2-chloro-4-trichloromethoxy-6-trifluoromethyl-1,3,5-triazine, 2,4-bis-trichloromethoxy-6-trichloromethyl-1,3,5-triazine, 2,4-bis-trichloromethoxy-6-trifluoromethyl-1,3,5-triazine, 2-fluoro-4-trichloromethoxy-6-trichloromethyl-1,3,5-triazine and 2-fluoro-4-tri-chloromethoxy-6-trifluoromethyl-1,3,5-triazine.

The novel trichloromethoxy-1,3,5-triazines II and the novel trifluoro- and chlorodifluoromethoxy-1,3,5-triazines I are valuable intermediates for the preparation of, for example, crop protection agents. For example, 2,4-dichloro- or 2,4-difluoro-6-trifluoromethoxy-1,3,5-triazine can be reacted with ammonia and methanol to give 2-amino-6-methoxy-4-trifluoromethoxy-1,3,5-triazine which reacts with 2-carbomethoxybenzenesulfonyl isocyanate to give herbicidal sulfonylureas. Subsequent reactions of this type are described in the applications P 40 24 761 (O.Z. 0050/41799) and P 40 24 754 (O.Z. 0050/41800) of the same date.

EXAMPLES

Example of the Preparation of Precursors

Example I.1

2,4-Difluoro-6-trichloromethoxy-1,3,5-triazine

A stream of gaseous chlorine was passed into a mixture of 300 g (2.041 mol) of 2,4-difluoro-6-methoxy-1,3,5-triazine and 0.3 g of a,al-azoisobutyronitrile at 130° C. with UV irradiation in such a way that the temperature reached 140°-145° C. within 2 hours. The progress of the reaction was checked by NMR spectroscopy and then chlorine was passed in at 135°-140° C. (external heating) for a further 3 hours. The precipitate was removed by filtration with suction and the filtrate was distilled under reduced pressure to yield 444 g (87% of theory) of the title compound of boiling point 40°-46° C./0.3 mbar.

II Reaction to give final products I

Example II.1

2,4-Difluoro-6-trifluoromethoxy-1,3,5-triazine

Half of 210 g (0.838 mol) of 2,4-difluoro-6-trichloromethoxy-1,3,5-triazine was added to a stirred mixture of 187.4 g (1.048 mol) of antimony trifluoride and 35.2 g (0.117 mol) of antimony pentachloride in such a way that the initial temperature of 110° C. rose to 125° C.; when reflux ceased, external heating was necessary while addition was continued. The mixture was stirred at 125°-130° C. for one hour, and a fraction boiling at 100°-105° C. was removed by distillation through a 25 cm packed column. After the reaction subsided, the remaining half of the trichloromethoxy compound was added dropwise within 30 minutes, and the fraction boiling at 100- 105° C. was continuously distilled out. The total reaction time was 3 hours. 134.4 g (79.8% of theory) of the title compound were obtained with $n_{24}{}^{24} = 1.3650$.

Example II.2

6-Chlorodifluoromethoxy-2,4-difluoro-1,3,5-triazine 210 g (0.838 mol) of 2,4-difluoro-6-trichloromethoxy-1,3,5-triazine were added within 10 minutes to 110 g (0.614 mol) of antimony trifluoride while stirring at 110° C. After addition of ¾ of 9.38 g (0.0313 mol) of antimony pentachloride, the mixture was heated to 145° C. and stirred for 1 hour. The remaining catalyst was added, and the mixture was stirred for a further 2 hours while a fraction boiling at 95°-105° C. was obtained through a 30 cm packed column: 20 g (11.8% of theory) of 2,4-difluoro-6-trifluoromethoxy-1,3,5-triazine. The residue was distilled without a column to yield 94.8 g (52% of theory) of the title compound of boiling point 125°-130° C.; $n_D{}^{24} = 1.4042$.

Example II.3

2,4-Dichloro-6-trifluoromethoxy-1,3,5-triazine 52 g (0.183 mol) of 2,4-dichloro-6-trichloromethoxy-1,3,5-triazine were added within 5 minutes to a stirred mixture of 40.9 g (0.229 mol) of antimony trifluoride and 7.03 g (0.0234 mol) of antimony pentachloride at 90° C., during which the temperature rose to 180° C. The mixture was then stirred at 170°-180° C. for 20 minutes, after which the crude product was distilled out at 90°-103° C./70 mbar. Another distillation yielded 32.3 g (75.5% of theory) of the title compound of boiling point 165°-173° C.

III Reactions of Compounds I to Give Herbicidal Sulfonylurea Derivatives

Example III.1

2-Amino-4-fluoro-6-trifluoromethoxy-1,3,5-triazine 4.4 g (0.259 mol) of gaseous ammonia were passed over the course of 45 minutes into a stirred mixture of 26.0 g (0.1293 mol) of 2,4-difluoro-6-trifluoromethoxy-1,3,5-triazine and 100 ml of tetrahydrofuran at −70° to −65° C. The mixture was then stirred for 2 hours at −70° C. and overnight while warming to 22° C. The residue from concentration under reduced pressure was stirred with water, filtered off with suction and washed. Drying yielded 22 g (85.9% of theory) of the title compound of melting point 138°-139° C.

EXAMPLE III.2

2,4-Bismethylamino-6-trifluoromethoxy-1,3,5-triazine and
2-methylamino-4-fluoro-6-trifluoromethoxy-1,3,5-triazine 5.9 g (0.189 mol) of methylamine were passed over the course of 30 minutes into a stirred mixture of 19. 0 g (0.0945 mol) of 2,4-difluoro-6-trifluoromethoxy-1,3,5-triazine and 100 ml of diethyl ether at −70° C. The mixture was stirred for 2 hours at −70° C. and overnight while warming to 22° C. The residue from concentration under reduced pressure was taken up in methylene chloride and washed with water. The solution was dried and chromatographed through a silica gel column. The first two fractions contained 5.0 g (25% of theory) of 2-methylamino-4-fluoro-6-trifluoromethoxy-1,3,5-triazine of melting point 68°-72° C., and fractions 4-7 yielded 10.7 g (51% of theory) of less soluble 2,4-bismethylamino-6-trifluoromethoxy-1,3,5-triazine of melting point 150°-152° C.

EXAMPLE III.3

2-Amino-4-chlorodifluoromethoxy-6-fluoro-1,3,5-triazine and
2,4-diamino-6-chlorodifluoromethoxy-1,3,5-triazine 7.8 g (0.46 mol) of ammonia were passed over the course of 45 minutes into a stirred mixture of 50.0 g (0.23 mol) of 2,4-difluoro-6-chlorodifluoromethoxy-1,3,5-triazine and 150 ml of tetrahydrofuran at −70° C. The mixture was stirred for 2 hours at −70° C. and overnight while warming to 22° C. It was concentrated under reduced pressure, washed with water and dried. The product was then loaded in methylene chloride onto a silica gel column and eluted with the same solvent. Fractions 1-8 yielded 21.5 g (43.6% of theory) of 2-amino-4-fluoro-6-chlorodifluoromethoxy-1,3,5-triazine of melting point 131°-133° C. Washing with ethyl acetate then yielded in fractions 9-14 the less soluble 2,4-diamino-6-chlorodifluoromethoxy-1,3,5-triazine (11.2 g, 23% of theory) of melting point 114° C.

Example III.4

2-Chlorodifluoromethoxy-4-fluoro-6-methylamino-1,3,5-triazine and
2,4-bismethylamino-6-chlorodifluoromethoxy-1,3,5-triazine 5.2 g (0.166 mol) of methylamine were passed over the course of 20 minutes into a stirred mixture of 18.1 g (0.083 mol) of 4-difluorochloromethoxy-2,6-difluoro-1,3,5-triazine at −70° C. The mixture was stirred for 2 hours at −70° C. and overnight while warming to 22° C. It was concentrated under reduced pressure, taken up in methylene chloride, washed with water and dried. Chromatography on silica gel yielded in the initial fractions 5.5 g (29% of theory) of 2-chlorodifluoromethoxy-4-fluoro-6-methylamino-1,3,5-triazine of melting point 62°-64° C. Subsequent fractions yielded 8.7 g (44% of theory) of 2.4-bismethylamino-6-chlorodifluoromethoxy-1,3,5-triazine of melting point 118°-120° C.

Example III.5

2-Amino-4-methoxy-6-trifluoromethoxy-1,3,5-triazine 9. 1 g (0. 05 mol) of 30% strength sodium methylate were added over the course of 15 minutes to a stirred mixture of 10 g (0.05 mol) of 2-amino-4-fluoro-6-trifluoromethoxy-1,3,5-triazine and 100 ml of methanol at 0° C. The mixture was stirred at 0° C. for one hour and then concentrated under reduced pressure, taken up in methylene chloride and extracted with water. Drying and concentration yielded 10.5 g (99% of theory) of the title compound of melting point 96°-101° C.

EXAMPLE III.6

2-Amino-4-chlorodifluoromethoxy-6-methoxy-1,3,5-triazine 8.4 g (0.047 mol) of 30% strength sodium methylate were added over the course of 15 minutes to a stirred mixture of 10 g (0.047 mol) of 2-amino-4-chlorodifluoromethoxy-6-fluoro-1,3,5-triazine and 100 ml of methanol at 0° C. The mixture was stirred at 0° C. for one hour and then concentrated under reduced pressure, taken up in methylene chloride and extracted with water. Drying and concentration yielded 10.4 g (98.5% of theory) of the title compound of melting point 109°-110° C.

Example III.7

2-Amino-4-ethoxy-6-trifluoromethoxy-1,3,5-triazine 2.3 g (0.093 mol) of 97% sodium hydride were added a little at a time to 300 ml of ethanol at 20°-35° C. and dissolved by stirring for 15 minutes. Then, while stirring at 0° C., 18.5 g (0.093 mol) of 2-amino-4-fluoro-6-trifluoromethoxy-1,3,5-triazin were added over the course of 10 minutes, and the mixture was stirred at 0° C. for 1 hour and at 22° C. overnight. The residue from concentration under reduced pressure was taken up in methylene chloride, extracted with water and dried. Concentration yielded 17.9 g (85.9% of theory) of the title compound of melting point 69°-71° C.

Example III.8

2-Amino-4-chlorodifluoromethoxy-6-ethoxy-1,3,5-triazine 1.2 g (0.047 mol) of 97% sodium hydride were added a little at a time to 150 ml of ethanol at 20°-35° C. and dissolved by stirring for 15 minutes. Then while stirring at 0° C., 10.0 g (0.047 mol) of 2-amino-4-chlorodifluoromethoxy-6-fluoro-1,3,5-triazine were added, and the mixture was stirred at 0° C. for 1 hour and at 22° C. overnight. The residue from concentration under reduced pressure was taken up in methylene chloride, extracted with water and dried. Concentration yielded 10.6 g (94.6% of theory) of the title compound of melting point 63°-65° C.

Example III.9

2-Amino-4-methylamino-6-trifluoromethoxy-1,3,5-triazine 3.5 g (0.111 mol) of methylamine were passed over the course of 20 minutes into a stirred solution of 11 g (0. 055 mol) of 2-amino-4-fluoro-6-trifluoromethoxy-1,3,5-triazine in 150 ml of tetrahydrofuran at 0° C. The mixture it was stirred at 0° C. for one hour and at 22° C. overnight. was then concentrated under reduced pressure, stirred with water and dried. 10.8 g (93.1% of theory) of the title compound of melting point 155°-157° C. (decomposition) were obtained.

Example III.10

2-Amino-4-chlorodifluoromethoxy-6-methylamino-1,3,5triazine 2.9 g (0.093 mol) of methylamine were passed over the course of 20 minutes into a stirred solution of 10 g (0.047 mol) of 2-amino-4-chlorodifluoromethoxy-6-fluoro-1,3,5-triazine in 150 ml of diethyl ether at 0° C. The mixture was stirred at 0° C. for one hour and at 22° C. overnight. Washing with water, drying and concentration yielded 9.4 g (89.5% of theory) of the title compound of melting point 143° C. (decomposition).

Example III.11

2-Amino-4-dimethylamino-6-trifluoromethoxy-1,3,5-triazine 5.0 g (0.111 mol) of dimethylamine were passed over the course of 20 minutes into a stirred solution of 11 g (0.055 mol) of 2-amino-4-fluoro-6-trifluoromethoxy-1,3,5-triazine in 150 ml of tetrahydrofuran at 0° C. The mixture was stirred at 0° C. for one hour and at 22° C. overnight. Concentration, washing with water and drying yielded 9.9 g (80.7% of theory) of the title compound of melting point 114°-118° C. (decomposition).

Example III.12

2-Amino-4-chlorodifluoromethoxy-6-dimethylamino-1,3,5-triazine 4.2 g (0.093 mol) of dimethylamine were passed over the course of 20 minutes into a stirred solution of 10 g (0.047 mol) of 2-amino-4-chlorodifluoromethoxy-6-fluoro-1,3,5-triazine in 150 ml of diethyl ether at 0° C. The mixture was stirred at 0° C. for one hour and at 22° C. overnight. Washing with water, drying and concentration yielded 9.8 g (87.8% of theory) of the title compound of melting point 130°-133° C. (decomposition).

Example III.13

Methyl 2-(4-methoxy-6-trifluoromethoxy-1,3,5-triazin-2-ylaminocarbonylaminosulfonyl)benzoate 3.6 g (0.015 mol) of 2-carbomethoxybenzenesulfonyl isocyanate in 4 ml of 1,2-dichloroethane were added over the course of 5 minutes to a stirred mixture of 3.15 g (0.015 mol) of 2-amino-4-methoxy-6-trifluoromethoxy-1,3,5-triazine and 150 ml of 1,2-dichloroethane at 22° C., and the mixture was stirred at 22° C. for 12 hours. It was then concentrated under reduced pressure and crystallized using 1:1 methyl tert-butyl ether/ petroleum ether, and the product was filtered off with suction and washed with petroleum ether to yield 5.1 g (75.4% of theory) of the title compound of melting point 149° C. (decomposition).

Example III.14

Sodium salt of methyl 2-(4-methoxy-6-trifluoromethoxy-1,3,5-triazin-2-ylaminocarbonylaminosulfonyl)benzoate 1.8 g (0.004 mol) of the compound from Example III.13 were suspended in 30 ml of methanol and, while stirring at 10°–15° C., 0.72 g (0.004 mol) of 30% strength sodium methylate solution was added. The clear solution was stirred for 10 minutes and then concentrated under reduced pressure, resulting in 1.9 g (100% of theory) of the title compound of melting point 118° C. (decomposition).

Example III.15

Ethyl 2-(4-methylamino-6-trifluoromethoxy-1,3,5-triazin-2-ylaminocarbonylaminosulfonyl)benzoate 3.1 g (0.012 mol) of 2-carboethoxybenzenesulfonyl isocyanate in 3 ml of methylene chloride were added over the course of 10 minutes to a stirred mixture of 2.5 g (0.012 mol) of 2-amino-4-methylamino-6-trifluoromethoxy-1,3,5-triazine and 150 ml of methylene chloride at 22° C., and the mixture was stirred at 22° C. for 30 hours. It was then concentrated under reduced pressure, stirred with methyl tert-butyl ether and filtered off with suction. Further washing with methanol and drying resulted in 3.8 g (67.4% of theory) of the title compound of melting point 182°–184° C. (decomposition).

We claim:

1. A substituted trichloromethoxy-1,3,5-triazine of the formula II

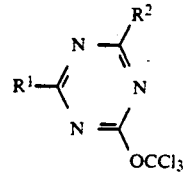

where $R^1$ and $R^2$ are each, independently of one another, hydrogen, fluorine or $C_1$–$C_4$-haloalkyl and $R^1$ is also trichloromethoxy.

2. 2,4-Difluoro-6-trichloromethoxy-1,3,5-triazine.

* * * * *